United States Patent [19]

Yen et al.

[11] Patent Number: 5,422,116
[45] Date of Patent: Jun. 6, 1995

[54] LIQUID OPHTHALMIC SUSTAINED RELEASE DELIVERY SYSTEM

[75] Inventors: Shau-Fong Yen, Atlanta; Kenneth W. Reed, Lawrenceville, both of Ga.

[73] Assignee: Ciba-Geigy Corporation, Ardsley, N.Y.

[21] Appl. No.: 198,924

[22] Filed: Feb. 18, 1994

[51] Int. Cl.$^6$ ............................................. A61K 47/00
[52] U.S. Cl. .................................. 424/427; 424/428; 424/485; 424/488; 514/777; 514/912; 514/913; 514/914; 514/915; 514/950; 514/954; 514/955; 514/964
[58] Field of Search ............... 424/427, 428, 484, 485, 424/488; 514/777, 912, 913, 914, 915, 950, 954, 955, 964

[56] References Cited

U.S. PATENT DOCUMENTS 5,318,780 6/1994 Viegas et al. .................... 424/427

Primary Examiner—Nathan M. Nutter
Attorney, Agent, or Firm—Norbert Gruenfeld

[57] ABSTRACT

Disclosed is a sustained release liquid aqueous ophthalmic delivery system and a method of providing a slow and sustained release of ophthalmic treating agents to the eye of a mammal which comprises administering to the eye of a said mammal an effective amount of a homogeneous liquid aqueous ophthalmic pharmaceutical composition, of pH between about 3.0 and about 6.2, which is administrable in drop form and which comprises an ophthalmically effective concentration of a said ophthalmic treating agent and about 0.05% to about 10% by weight of the polymer chitosan; said polymer consisting essentially of (A) monomeric $\beta(1\rightarrow 4)$-D-glucosamine linked units and of
(B) monomeric $\beta(1\rightarrow 4)$-D-glucosamine linked units which are scattered randomly in the molecule of the polymer, the numerical proportions of A and B being from about 60 to about 99% of A and about 1 to about 40% of B, the viscosity rating being from about 3 to about 3000 cps; in which method, upon contact with the higher pH of the ocular fluid, said liquid formulation is converted to a stiff gel from which the ophthalmic treating agent is slowly released over a prolonged period of time.

21 Claims, No Drawings

LIQUID OPHTHALMIC SUSTAINED RELEASE DELIVERY SYSTEM

FIELD AND BACKGROUND OF THE INVENTION

There is a need for a liquid ophthalmic drug delivery system which is administrable to the eye in convenient drop form and which at the same time provides a prolonged ocular residence of the topically administered drug so as to maximize the topical duration of action and minimize any systemic effects.

As is well-known in the art, there is little chance of absorption of an ophthalmic drug administered to the eye in view of the fast turnover of tear fluid resulting in the drug being rapidly drained away from the eye. Therefore a vehicle is required which remains in the ocular area and retains the ophthalmic drug for a slow release thereof.

The present invention relates to the finding that an advantageous prolonged and sustained release of ophthalmic drugs into the eye can be achieved with a chitosan containing liquid ophthalmic aqueous formulation thereof which is administered at a pH of from about 3.0 to 6.2 in convenient drop form.

Chitin is a naturally occurring biopolymer of monomeric $\beta(1\rightarrow 4)$-N-acetyl-D-glucosamine linked units of varying molecular weight. N-deacetylation of chitin leads to chitosan, e.g. as described in U.S. Pat. No. 3,911,098 which is incorporated herein by reference.

Chitosan is partially to substantially deacetylated chitin, and in contrast to chitin contains free amine ($NH_2$) groups along the polymer chain.

Chitosan is, due to the presence of the free amine groups which can be protonated under acidic conditions, classified as a cationic polymer. According to U.S. Pat. No. 3,953,608, chitosan "presents the major drawback of being insoluble in an alkaline medium ". There is no appreciation or suggestion in the art that the insolubility of chitosan in an alkaline medium can in fact be used to advantage for the preparation of ophthalmic formulations so as to provide a sustained release of ophthalmic treating agents into the eye.

SUMMARY OF THE INVENTION

The instant invention is directed to a method of providing a slow and sustained release of an ophthalmic treating agent using a liquid aqueous ophthalmic composition comprising chitosan, also to liquid ocular delivery systems comprising chitosan for delivering a said ophthalmic treating agent, and also to the resulting liquid ophthalmic compositions comprising chitosan and the ophthalmic treating agents.

The object of the invention is to provide sustained and prolonged release of ophthalmic treating agents. A further object of the invention is to provide a liquid aqueous ophthalmic delivery system which is administrable to the eye in drop form but results in an advantageous prolonged ocular residence of the topically administered ophthalmic treating agent so as to maximize the time available for topical action.

Chitosan as used in the present invention refers to a polymer consisting essentially of monomeric $\beta(1\rightarrow 4)$-D-glucosamine (A) linked units and of monomeric $\beta(1\rightarrow 4)$-N-acetyl-D-glucosamine (B) linked units which are scattered randomly in the molecule of the polymer, the numerical proportions of A and B being from about 60 to about 99% of A and about 1 to about 40% of B, the viscosity rating of the polymer being from about 3 to about 3000 cps.

It has now been found that chitosan is particularly suitable, especially under conditions specified herein, as an ocular release-rate controlling agent in sustained release liquid ophthalmic drug formulations. Although administrable in convenient drop form such formulations achieve an advantageous residence time in the eye with prolonged and sustained release of the ophthalmic treating agent contained therein into the eye. It has been found that chitosan is a beneficial pH-dependent ocular release rate controlling agent for the preparation of liquid ophthalmic drug formulations which can be administered at a pH somewhere between about 3.0 and about 6.2 and which are converted to viscous stiff gels on contact with the higher physiological pH of the ocular fluid after administration to the cul-de-sac of the eye.

DETAILED DESCRIPTION OF THE INVENTION

More specifically the instant invention is directed to a method of providing a slow and sustained release of one or more ophthalmic treating agents to the eye of a mammal which comprises administering to the eye of a said mammal an effective amount of a homogeneous liquid aqueous ophthalmic pharmaceutical composition, of pH between about 3.0 and about 6.2, which is adminstrable in drop form and which comprises an ophthalmically effective concentration of a said ophthalmic treating agent and about 0.05% to about 10% by weight of the polymer chitosan; said polymer consisting essentially of (A) monomeric $\beta(1\rightarrow 4)$-D-glucosamine linked units and of (B) monomeric $\beta(1\rightarrow 4)$-N-acetyl-D-glucosamine linked units which are scattered
randomly in the molecule of the polymer, the numerical proportions of A and B being from about 60 to about 99% of A and about 1 to about 40% of B, and the viscosity rating of the polymer being from about 3 to 3000 cps; in which method, upon contact with the higher pH of the ocular fluid, said liquid formulation is converted to a stiff gel from which the ophthalmic treating agent is slowly released over a prolonged period of time.

The resulting stiff gel adheres to the ocular tissue for a length of time sufficient to provide a prolonged bioavailability of the ophthalmic treating agent into the eye.

Chitosan as used in the present invention refers to polymers of varying molecular weight, from about 10 thousand to about 10 million, and the polymers are characterized by a corresponding viscosity rating.

Chitosan in various forms is commercially available or can be prepared by deacetylation of chitin, e.g. as described in U.S. Pat. No. 3,953,068, Commercial sources of chitosan are e.g. Nova Chem Limited, Anndale, Halifax, Nova Scotia, Canada; Vanson Company, Redmond, Was., U.S.A.; and Protan, Inc., Commack, N.Y., U.S.A.

The chitosan is also characterized as to the proportion of N-acetyl-D-glycosamine units and D-glucosamine units, and such is expressed as the degree of deacetylation of the fully acetylated polymer chitin. Preferably the degree of deacetylation ranges from 70 to 90%, meaning that the proportion of N-acetyl-D-glucosamine units and D-glucosamine units in the chitosan is 10 to 30% of N-acetyl-D-glucosamine units and 70 to 90% of D-glucosamine units. The degree of deacetylation (free mine) can be determined by dissolving a sample in dilute hydrochloric acid, and back titrating the excess acid with dilute sodium hydroxide.

The viscosity rating is the measured viscosity of a solution of one percent of the chitosan polymer in one percent acetic acid (Brookfield LVT viscometer, spindle #2, 30 rpm, 20° C.). The viscosity ratings of the chitosan polymer range from about 3 to about 3000 cps, preferably from about 50 to 2000 cps, advantageously from about 100 to 1000 cps.

In general, the higher the viscosity rating the higher the molecular weight of the chitosan polymer.

For purposes of the present invention, a stiff gel is characterized by an elastic modulus which exceeds 1000 Pas under 1 Pas of shear stress measured at 0.1 Hz of oscillation frequency at 25° C.

In general, the viscosity of the chitosan containing ophthalmic formulations of the invention increases with increasing pH due to e.g. the reversible interconversion of the ammonium salt form of the D-glucosamine units within the polymer to the free amine form thereof, thus resulting in a more water insoluble form of the polymer carrier. Since this interconversion is an equilibrium process and hence time dependent, the chitosan containing formulation must be administered to the cul-de-sac of the eye in order for the conversion to a stiff gel to occur.

The preferred pH to obtain a liquid formulation which can be administered in drop form depends on the viscosity rating and the molecular weight of the chitosan, the concentration of the chitosan and the ratio of D-glucosamine to N-acetyl-D-glucosamine units in the particular chitosan. The pH is adjusted according to known procedures with either mineral or organic acid (e.g. hydrochloric acid, acetic acid) or mineral or organic base (e.g. sodium hydroxide or an mine) as required, so as to obtain a formulation with a viscosity suitable for administration to the eye in drop form. The appropriate pH ranges between about 3.0 and about 6.2.

Ophthalmic treating agents (drugs) which can be incorporated in the ophthalmic formulations are those well known in the art, for instance an ocular non-steroidal antiinflammatory drug, an ocular steroidal antiinflammatory agent, an ocular antibacterial agent, an ocular antifungal agent, an ocular antiviral agent, an anti-glaucoma agent, a miotic agent, an ocular decongestant, an antihistamine, a prostaglandin, a transdermal growth factor, an ocular nutrient or a demulcent. Such are used at an effective concentration ranging from about 0.001% to about 10% by weight, preferably from about 0.01% to about 5% by weight.

Typical non-steroidal antiinflammatory agents are for instance diclofenac, flurbiprofen, suprofen, piroxicam or ketorolac, and ophthalmologically acceptable salts thereof.

Typical steroidal antiinflammatory agents are for instance prednisolone acetate, prednisolone, fluorometholone, fluorometholone acetate, hydrocortisone, hydrocortisone acetate or dexamethasone.

Typical antibacterial agents are for instance chloramphenicol, ciprofloxacin, gentamycin, norfloxacin, sulfacetamide, tetracycline, tobramycin, vancomycin, ticarcillin, polymyxin B, penicillin G, neomycin, moxalactam, methicillin, kinamycin, gentamycin, erythromycin, colistimethate, clindamycin, cefazolin, carbenicillin, bacitracin, ampicillin or amikacin, and ophthalmologically acceptable salts thereof.

Typical antifungal agents are for instance amphotericin B, flucytosine, natamycin or myconazole.

Typical antiviral agents are for instance idoxuridine, trifluridine, vidarabine, acyclovir or ganciclovir.

Typical miotic agents are for instance carbachol, pilocarpine, physostigmine, demecarium, echothiophate or isoflurophate, and ophthalmologically acceptable salts thereof.

Typical antiglaucoma agents are for instance dipiverfrin, epinephrine, hydralazine, pilocarpine, carbachol, betaxolol, carteolol, lerobunolol, metipranolol, timolol, isosorbide, azetazolamide or methazolamide, and ophthalmologically acceptable salts thereof.

Typical ocular decongestants are for instance naphazoline, phenylephrine or tetrahydrozoline, and ophthalmologically acceptable salts thereof.

Typical ocular nutrients are for instance various forms of Vitamin A such as Vitamin A acid, Vitamin A alcohol, Vitamin A acetate or Vitamin A palmitate.

Typical demulcents are for instance carboxymethylcellulose sodium, dextran 70, gelatin, glycerin, hydroxyethylcellulose, hydroxypropylmethylcellulose, methylcellulose, polyethylene glycol 300, polyethylene glycol 400, polysorbate 80, polyvinyl alcohol, povidone, propylene glycol and the like.

The instant invention also provides for a sustained release liquid aqueous ophthalmic delivery system for ophthalmic treating agents, of pH between about 3.0 and about 6.2, which comprises about 0.05% to about 10% by weight of the polymer chitosan as the release rate controlling agent, said polymer consisting essentially of (A) monomeric $\beta(1\rightarrow 4)$-D-glucosamine linked units and of (B) monomeric $\beta(1\rightarrow 4)$-N-acetyl-D-glucosamine linked units which are scattered randomly in the molecule of the polymer, the numerical proportions of A and B being from about 60 to about 99% of A and about 1 to about 40% of B, and the viscosity rating of the polymer being from about 3 to 3000 cps; in which method, upon contact with the higher pH of the ocular fluid, said liquid formulation is convened to a stiff gel from which the ophthalmic treating agent incorporated therein is slowly released over a prolonged period of time.

The instant invention is also directed to liquid aqueous ophthalmic pharmaceutical compositions, of pH between about 3.0 and about 6.2, which are administrable in drop form, and which comprise about 0.05% to about 10% by weight of the polymer chitosan as the release rate controlling agent and one or more ophthalmic treating agents at an effective concentration; said polymer consisting essentially of (A) monomeric $\beta(1\rightarrow 4)$-D-glucosamine linked units and of (B) monomeric $\beta(1\rightarrow 4)$-D-glucosamine linked units which are scattered randomly in the molecule of the polymer, the numerical proportions of A and B being from 60 to 99% of A and about 1 to 40% of B, and the viscosity rating of the polymer being from about 3 to about 3000 cps; said pharmaceutical compositions upon contact with the higher pH of the ocular fluid being convened to a stiff gel so as to provide a slow release of the ophthalmic treating agent(s) into the eye for a prolonged period of time.

The ophthalmic formulations are administered as liquid formulations wherein the composition is a low viscosity liquid administrable in drop form which becomes a high viscosity gel (a stiff gel) upon instillation in the eye.

The liquid ophthalmic compositions which are administrable in drop form are formulated at a pH below physiological pH at which amine groups of chitosan are substantially in the protonated form. When delivered to the eye and as insolubilization of the polymer occurs at the higher (and more basic) physiological pH of the eye, the liquid formulations are converted to a viscous stiff gel which adheres to the corneal surface for a length of time sufficient to provide a prolonged bioavailability of the ophthalmic treating agent to the eye.

Factors affecting the viscosity include the properties of the chitosan used (viscosity rating, molecular weight, proportion of acetylated to non-acetylated D-glucosamine units), the concentration of the chitosan and the pH of the formulation.

A major factor affecting the viscosity of the chitosan containing ophthalmic treating agent formulations is their pH, and such can be adjusted according to methods well known in the art, e.g. with an acid such as hydrochloric acid to decrease the pH, or with a base such as sodium hydroxide to raise the pH. The pH is adjusted so as to obtain a viscosity suitable for administration in drop form. Generally, the higher the pH the higher the viscosity due to the lower water solubility of the polymer as more unprotonated free amine groups are then present. The highest possible pH at which the composition can be administered in drop form is selected so that any irritation to the eye is minimized.

Preferred pH of the formulations ranges from about 4.0 to about 6.0, advantageously 4.5 to 6.0.

Preferred concentration of chitosan ranges from about 0.1 to about 5%, advantageously from about 0.5 to about 4%. In general, the higher the viscosity rating of the chitosan the lower is the concentration used.

The viscosity of the chitosan containing formulations which are administrable in drop form is between about 10 cps and about 100,000 cps at a shear rate of 1 sec$^{-1}$, preferably between about 100 to 80,000 cps, advantageously between about 1,000 and 80,000 cps as measured using the Bohlin CS Rheometer (Plate-Plate Geometry). The viscosity of the present formulations remains substantially constant over a wide range of shear rates.

Preferred as release controlling agent is chitosan having a viscosity rating of about 100 to 1000 cps, with a degree of deacetylation of about 80 to 90%, used at a concentration of about 0.5% to 5% and a pH of about 4.5 to about 6.0.

In addition to the active ingredient and chitosan, the compositions of the present invention may include other components, for example ophthalmically acceptable preservatives, tonicity agents, cosolvents, wetting agents, complexing agents, buffering agents and surfactants well known in the art.

The resulting ophthalmic formulations may have a tonicity substantially equivalent to a 0.45% to 1.8% sodium chloride solution, preferably substantially equivalent to a 0.5% to 1% sodium chloride solution, advantageously to a 0.9% sodium chloride solution.

Suitable tonicity enhancing agents include alkali metal halides (preferably sodium or potassium chloride), mannitol, sorbitol and the like.

Sufficient tonicity enhancing agent is advantageously added so that the formulation to be instilled into the eye is hypotonic or substantially isotonic, that is of the same tonicity as physiological fluids, e.g. substantially equivalent in tonicity to a 0.9% aqueous sodium chloride solution.

Preferred osmolality ranges from about 240–340 mosmol/Kg, measured according to standard methodology.

Suitable preservatives are those generally used in the an e.g. benzalkonium chloride, thimerosal, phenethyl alcohol, methylparaben, propylparaben, chlorhexidine, sorbic acid and the like. Hydrogen peroxide or a source thereof along with a hydrogen peroxide stabilizer as described in European patent application No. 354,186 published Feb. 7, 1990 may also be used as preservative. Furthermore, ethylenediaminetetraacetic acid may be added as stabilizer.

Suitable cosolvents are for example glycerin, propylene glycol and polyethylene glycol.

Suitable complexing agents are for example caffeine, polyvinylpyrrolidone, $\beta$-cyclodextrin or hydroxypropyl-$\beta$-cyclodextrin. Suitable surfactants or wetting agents are for example sorbitan esters, polysorbates such as polysorbate 80, tromethamine, lecithin, cholesterol, tyloxapol and the like.

The suitability of the formulations of the instant invention for controlled release (e.g. sustained and prolonged delivery) of an ophthalmic treating agent in the eye can be determined by various procedures known in the art, e.g. as described in Journal of Controlled Release 6, 367-373 (1987) and variations thereof.

Ophthalmic residence (retention) time in the rabbit can be determined using gamma detection as follows:

A Ludium 2200 pulse height analyzer with a Ludium 1"×1"NaI (Ti) high energy end-window gamma scintillator is employed. The probe is wrapped in 3 mm of lead (15 half value layer of Pb for Tc-99m) sheet and the detector face is covered with 3 mm of lead after a 1.5 cm collinator opening is cut in the lead. The same detector to eye distance (2 cm) for data collection is maintained with a distance piece fitted to the end of the detector. The minimum detectable activity for the system is $1.39 \times 10^{-4} \mu Ci$ using a Cobalt-57 disc as the reference source.

Prior to vehicle instillation, the probe is placed over the animal's eye and ink marks are made on the rabbit to correspond to 3 similar marks on the styrofoam distance piece. These marks are lined up for each subsequent data collection assuring constant counting geometry. Using an Eppendoff Pipette 30 ul of Sodium Pertechnetate-99mTc in 0.9% saline or chitosan solution are instilled into the lower left eyelid. Chitosan polymers are directly radiolabeled with 99 mTc using standard radiopharmaceutical techniques.

Upon completion of test vehicle instillation, the lower eyelid is closed once to effect mixing. Further mixing of the Technetium-99m solution is achieved by the rabbit's natural blinking tendencies. Data collection is begun immediately after instiillation. The mean amount of radioactivity administered is 20.94±4.6 uCi.

Activity is then measured for each animal at various time intervals post instillation and the percent activity retained is calculated. Each count is obtained for 6 seconds. Background counts are taken at the beginning of each procedure and range from 5–8 counts/6 seconds with a mean of 6.8±2.61 counts/6 seconds.

Illustrative of the invention, the average percent of the ocular retention of radioactivity from a normal saline vehicle and the chitosan containing vehicle of example 15 at 5, 30, 60 and 120 minutes post-instillation to the eye of 8 rabbits is as follows:

| | Average % Retention (Mean ± SE) | | | |
|---|---|---|---|---|
| Vehicle | 5 minutes | 30 minutes | 60 minutes | 120 minutes |
| Normal Saline | 16.55 ± 5.52 | 7.61 ± 4.67 | 6.35 ± 4.54 | 5.29 ± 2.94 |
| Chitosan (Example 15) | 71.18 ± 21.47 | 45.28 ± 15.49 | 33.22 ± 10.68 | 22.02 ± 8.99 |

The greater retention of radioactivity with the chitosan vehicle is indicative of a greater residence time in the eye for the chitosan containing vehicle. Significant radioactivity is retained in the eye over a period of at least two hours, compared to no significant retention using a normal saline vehicle at 30 minutes post administration.

Further illustrative of the invention, the sustained release of the ophthalmic drug in a chitosan containing formulation can be determined by measuring the effect of a particular ophthalmic treating agent, e.g. the miotic effect (contraction of the pupil) with pilocarpine.

The effect of pilocarpine on pupil diameter in healthy Dutch belted rabbits (2–3 Kg) having normal intraocular pressure is determined as follows:

Pupil diameter (mm) is measured horizontally, under constant illumination, in normal rabbits. Baseline readings are taken at both treated and untreated (contralateral) eyes before drug administration and post drug determinations are made at 20, 30, 40, 60, 120, 180, 240 and 300 minutes respectively.

The % miosis (contraction of the pupil) compared to baseline is calculated as follows:

$$\% \text{ Miosis} = \frac{((\text{Baseline Diameter}) - (\text{Measured Diameter})) \times 100}{(\text{Baseline Diameter})}$$

The results in rabbits using 2% pilocarpine hydrochloride in the chitosan containing formulation of example 14 and a 2% pilocarpine hydrochloride marketed sustained release product (Spersacarpine ® 2%) as a control are as follows:

| Time after administration minutes | Chitosan Formulation Pupil diameter (Mean ± SE, in mm) | % Miosis | Spersacarpine ® % Miosis |
|---|---|---|---|
| 0 (Baseline) | 6.9 ± 0.2 | 0 | 0 |
| 20 | 2.6 ± 0.2 | 64 | 47 |
| 30 | 3.0 ± 0.0 | 56 | 45 |
| 40 | 3.3 ± 0.1 | 51 | 41 |
| 60 | 4.0 ± 0.0 | 42 | 32 |
| 120 | 4.7 ± 0.2 | 32 | 25 |
| 180 | 5.4 ± 0.1 | 21 | 10 |
| 240 | 5.9 ± 0.1 | 14 | 6 |
| 300 | 6.4 ± 0.1 | 7 | — |

Spersacarpine ® 2% is 2% pilocarpine hydrochloride in a hydroxypropylmethylcellulose vehicle, marketed by Dispersa AG, Hettlingen, Switzerland.

The results demonstrate that miotic activity of pilocarpine is maintained over a period of 4 to 5 hours using a chitosan vehicle, as compared to a commercial 2% pilocarpine hydrochloride sustained release formulation having a duration of miotic activity of only 3 to 4 hours. A significant increase in miotic activity is obtained when 2% pilocarpine hydrochloride is formulated with chitosan rather than hydroxypropylmethylcellulose.

The sustained release of active ingredient, e.g. pilocarpine from a chitosan containing vehicle compared to release from a saline vehicle can be determined in vitro in a diffusion-cell system as follows:

A standard Franz diffusion cell, flat ground glass with 15 mm-diameter orifice is used. A Nylon membrane with 0.45 μm pore size (Gelman Sciences, Inc., Ann Arbor, MI) is used.

Dulbeco's Phosphate Buffered Saline (KCl, 200 mg/l; KH$_2$PO$_4$, 200 mg/l; NaCl, 8,000 mg/l and Na$_2$HPO$_4$·7H$_2$O, 2,160 mg/l) is used as the receptor medium. Samples are collected at intervals of 5, 15, 30, 60, 90, 120, 150, 210, 270, 390, 510, 690 and 1060 minutes for analysis.

One gram of 1% pilocarpine hydrochloride either in 2% chitosan PTL-122 (viscosity rating of 980 cps) at pH 5.0, or in saline is evenly spread on the membrane.

A microette automated sampler (Hanson Research Corporation, Chatsworth, CA); an auto injector and an HPLC system equipped with a Phenomenex Selectosil 5 C18 100A 25 cm×4.0 mm column and a Detector with wavelength set at 216 nm are utilized for sampling and analysis.

The lower part of a standard Franz diffusion cell is filled with receptor phase medium. The top part of the cell, holding the membrane and the sample, is placed membrane-side down on the bottom of the cell and placed in position with clamps. The medium is equilibrated to 35° C. The Hanson Microette automated sampler is interfaced with the diffusion cell, and a 1.5 ml aliquot is withdrawn from the middle part of the cell at a programmed time interval and transferred into a sample carousel.

The HPLC analysis of pilocarpine is carded out using a Phenomenex Setectosil 5 C 18 column. Samples are eluted using an ioscratic mobile phase consisting of water:H$_3$PO$_4$:methanol:triethylamine (979:6: 10:5) at ambient temperature and a flow at 1.2 ml/minute. The concentration of pilocarpine in the sample is calculated using a standard of known concentration.

Illustrative of the invention, pilocarpine is released over a prolonged period of time, over a period of about 500 minutes from the chitosan vehicle. In contrast thereto, pilocarpine is only released over a period of 250 minutes from the control saline vehicle.

The ophthalmic chitosan containing ophthalmic formulations of the present invention comprise an active ingredient at a concentration so that an effective amount thereof is contained in a drop (about 25–50 μl) of the formulation.

The effective concentration of the active ingredient is either known in the art or can be easily determined by one skilled in the art. Typically the effective concentration ranges from about 0.001% to about 10% of the active ingredient, preferably from about 0.01% to about 5%, for example, about 1% for pilocarpine hydrochloride, about 0.1% for diclofenac sodium, about 0.25% for timolol maleate, about 0.3% for gentamicin sulfate and the like.

Typically, one drop of the chitosan containing ophthalmic drug formulation is administered into the cul-de-sac of the eye of a mammal, including man, in need of treatment therewith, about 1 to 4 times a day. On exposure to the physiological pH of about 7, the liquid drop administered to the eye becomes a stiff gel which remains within the lower cul-de-sac of the eye from which the active ingredient is slowly released.

The following examples are presented for illustrative purposes and are not intended to limit the scope of the invention.

The grades of chitosan used are classified according to a viscosity rating corresponding to the measured viscosity of one percent chitosan in one percent acetic acid (Brookfield LVT viscometer, spindle #2, 30 rpm, 20° C.).

The commercial grades of chitosan in the instant illustrative examples are defined as having viscosity ratings of 180 cps (PTL-134), 370 cps (PTL-133), and 980 cps (PTL-122).

EXAMPLE 1

| Example 1 | |
| --- | --- |
| Chitosan PTL-122 | 12.56 g |
| Concentrated hydrochloric acid | 6.3 g |
| Pilocarpine hydrochloride | 2.7 g |
| Water | 251 g |
| Sodium hydroxide 1% | q.s. to pH 5.0 |
| Mannitol | q.s. to 280–320 mOsm |

The resulting ophthalmic formulation contains 1% pilocarpine hydrochloride and 4.65% of chitosan (PTL-122).

The chitosan PTL-122 grade (obtained from Vanson Company, Redmond, Wash.) is about 80% deacetylated with a 1% solution of the chitosan PTL-122 in 1% acetic acid having a viscosity of 980 cps.

The chitosan is dissolved in 251 g of dilute hydrochloric acid (containing 6.3 g of concentrated hydrochloric acid). The pH is adjusted to 5.0 with (10%) sodium hydroxide solution. The pilocarpine hydrochloride is added, followed by sufficient mannitol to adjust osmolarity to 280–320 mOsm.

EXAMPLE 2

| Example 2 | |
| --- | --- |
| Chitosan PTL-134 | 20.0 g |
| Hydrochloric acid 0.695% | 500 ml |
| Pilocarpine hydrochloride | 10.0 g |
| Sodium chloride | 5.0 g |
| Sodium hydroxide 1% | q.s to pH 5.0 |

The resulting ophthalmic solution contains 2% pilocarpine hydrochloride and 4% chitosan PTL-134.

The chitosan PTL 134 grade (obtained from Vanson Company) is about 80% deacetylated with a 1% solution in 1% acetic acid having a viscosity of 180 cps.

The chitosan is dissolved in the dilute hydrochloric acid. Pilocarpine hydrochloride is added, followed by sodium chloride and the pH is adjusted to 4.85 with (10%) sodium hydroxide.

EXAMPLE 3

| Example 3 | |
| --- | --- |
| Chitosan PTL-133 | 20.0 g |
| Hydrochloric acid (0.7%) | 480.0 ml |
| Pilocarpine hydrochloride | 5.0 g |
| Sodium hydroxide 1% | q.s. to pH 4.5 |
| Sorbitol | q.s. to 280–320 mOsm |

The resulting ophthalmic formulation contains 1% pilocarpine hydrochloride and chitosan PTL-133.

The chitosan PTL-133 grade (obtained from Vanson Company) is about 85% deacetylated with a 1% solution in 1% acetic acid having a viscosity of about 370 cps.

The chitosan is dissolved in the dilute hydrochloric acid. Pilocarpine hydrochloride is added and the osmolarity is adjusted to 280-320 mOsm with sorbitol and the pH is adjusted to 4.5 with (10%) sodium hydroxide.

EXAMPLE 4

| Example 4 | |
| --- | --- |
| Chitosan PTL-133 | 40 g |
| Acetic acid 1% | 960 ml |
| Pilocarpine hydrochloride | 20 g |
| Sodium chloride | q.s. to 270–330 mOsm |
| Sodium hydroxide 1% | q.s. to pH 4.5 |

The chitosan is dissolved in dilute acetic acid. Pilocarpine hydrochloride is added. The osmolarity is adjusted to 270–330 mOsm with sodium chloride and the pH is adjusted to 4.5 with 5% sodium hydroxide.

The resulting ophthalmic formulation contains 2% pilocarpine hydrochloride and chitosan PTL-133.

EXAMPLE 5

| Example 5 | |
| --- | --- |
| Chitosan PTL-133 | 20 g |
| Hydrochloric acid 0.7% | 960 ml |
| Pilocarpine hydrochloride | 10 g |
| Benzalkonium chloride | 0.1 g |
| Sodium Hydroxide 1% | q.s. to pH 5.0 |
| Mannitol | qs. to 280–320 mOsm |

The resulting ophthalmic formulation contains 1% pilocarpine hydrochloride and chitosan PTL-133.

The chitosan is dissolved in dilute hydrochloric acid, pilocarpine hydrochloride and benzalkonium chloride are added. The pH is adjusted to 5 with 5% sodium hydroxide and the osmolarity is rendered isotonic with mannitol.

EXAMPLE 6

| Example 6 | |
| --- | --- |
| Chitosan PTL-134 | 25 g |
| Hydrochloric acid 0.93% | 500 ml |
| Timolol maleate | 1.31 g |
| Sodium hydroxide 1% | q.s. to pH 4.5 |
| Sorbitol | q.s. to 280–320 mOsm |

The resulting ophthalmic formulation contains 0.25% timolol maleate and 4.65% chitosan PTL-134. The chitosan is dissolved in the dilute hydrochloric acid, timolol maleate is added. The pH is then adjusted to pH 4.5 with dilute sodium hydroxide and the osmolarity is rendered isotonic with sorbitol.

EXAMPLE 7

| Example 7 | |
| --- | --- |
| Chitosan PTL-134 | 40 g |
| Acetic acid 0.8% | 950 ml |
| Diclofenac sodium | 1.0 g |
| Hydrochloric acid 1% | q.s. to pH 4.0 |
| Sodium chloride | q.s. to 280–320 mOsm |

The resulting ophthalmic formulation contains 0.1% diclofenac sodium and 4% of chitosan PTL-134.

The chitosan is dissolved in the dilute acetic acid (0.8%), diclofenac sodium is added. The pH is adjusted to 4.0 with the dilute hydrochloric acid and rendered isotonic with sodium chloride.

EXAMPLE 8

| Example 8 | |
|---|---|
| Chitosan PTL-122 | 20 g |
| Hydrochloric acid 1% | 960 ml |
| Sodium hydroxide 1% | q.s. to pH 5.0 |
| Sodium chloride | q.s. to 280–320 mOsm |

The resulting ophthalmic vehicle contains 2% chitosan PTL-122.

The chitosan is dissolved in the dilute hydrochloric acid, sufficient sodium hydroxide is added to adjust pH to 5.0 and mannitol is added to adjust osmalarity to 280–320 mOsm.

EXAMPLE 9

| Example 9 | |
|---|---|
| Gentamycin sulfate | 3 g |
| Benzalkonium chloride | 0.1 g |
| Vehicle of Example 8 | 997 ml |

Gentamycin sulfate and benzalkonium chloride are added to the vehicle of example 8.

The resulting ophthalmic formulation contains 0.3% gentamycin sulfate and 2% chitosan PTL-122.

EXAMPLE 10

| Example 10 | |
|---|---|
| Fluorometholone (Micronized) | 2.5 g |
| Polysorbate 80 | 0.5 g |
| Edetate disodium | 0.05 g |
| Vehicle of example 8 | 997 ml |

The three ingredients are added to the chitosan vehicle. The resulting ophthalmic formulation contains 0.25% fluorometholone, 0.05% polysorbate 80 and 2% chitosan PTL-122.

EXAMPLE 11

| Example | |
|---|---|
| Chitosan PTL-122 | 20 g |
| Citric acid (0.01%) | 950 ml |
| Gentamicin sulfate | 3 g |
| Potassium chloride | q.s. to 280–320 mOsm |
| Benzalkonium chloride | 0.2 g |
| Hydrochloric acid 1% | q.s. to pH 5.0 |

The chitosan is dissolved in dilute citric acid solution. The pH is adjusted to 5.0 with dilute hydrochloric acid. The gentamicin sulfate is added, the solution is rendered isotonic with potassium chloride, and benzalkonium chloride is added.

The resulting ophthalmic formulation contains 0.3% gentamicin sulfate and 2% chitosan PTL-122.

EXAMPLE 12

| Example 12 | |
|---|---|
| Chitosan PTL-122 | 2.0 g |
| Sodium chloride | 0.25 g |
| Water | 98.0 g |
| Sodium hydroxide | q.s. to pH 5 |

The first two ingredients are dissolved in water, and sufficient sodium hydroxide is added to adjust pH to 5.0. The resulting vehicle contains 2% chitosan PTL-122.

EXAMPLE 23

| Example 13 | |
|---|---|
| Chitosan PTL-133 | 4.0 g |
| Sodium chloride | 0.30 g |
| Sodium hydroxide | q.s. to pH 5 |
| Water | 95 g |

The chitosan (degree of deacetylation about 85%) is dissolved in the water containing 0.30 g of sodium chloride. The pH is adjusted to 5.0 with sodium hydroxide. The resulting vehicle contains 4% chitosan PTL-133.

EXAMPLE 14

| Example 14 | |
|---|---|
| Chitosan PTL-122 | 20 g |
| Acetic Acid 1% | 975 g |
| Sodium chloride | q.s. to 270–330 mOsm |
| Sodium hydroxide 10% | q.s. to pH 4.5 |
| Pilocarpine hydrochloride | 20 g |

The resulting ophthalmic formulation contains 2% pilocarpine hydrochloride and chitosan PTL-122.

The chitosan is dissolved in the dilute acetic acid. Pilocarpine hydrochloride is added and the osmolarity is adjusted to 280–320 mOsm with sodium chloride and the pH is adjusted to 4.5 with 10% sodium hydroxide solution.

EXAMPLE 15

| Example 15 | |
|---|---|
| Chitosan PTL-133 | 22 g |
| Hydrochloric acid 1% | 974 g |
| Mannitol | q.s. to 270–330 mOsm |
| Sodium hydroxide 10% | q.s. to pH 6.2 |

The resulting ophthalmic vehicle contains 2.2% chitosan PTL-133.

The chitosan is dissolved in the dilute hydrochloric acid. Sodium hydroxide solution is added to adjust pH to 6.2 and mannitol is added to adjust osmolarity to 270–330 mOsm.

What is claimed is:

1. A method of providing a slow and sustained release of an ophthalmic treating agent to the eye of a mammal which comprises administering to the eye of a said mammal an effective amount of a homogeneous liquid aqueous ophthalmic pharmaceutical composition, of pH between about 3.0 and about 6.2, which is administrable in drop form and which comprises an ophthalmically effective concentration of a said ophthalmic treating agent and about 0.05% to about 10% by weight of the polymer chitosan as the release rate controlling agent; said polymer consisting essentially of
(A) monomeric β(1→4)-D-glucosamine linked units and of
(B) monomeric β(1→4)-N-acetyl-D-glucosamine linked units which are scattered randomly in the molecule of the polymer, the numerical proportions of A and B being from about 60 to about 99% of A and about 1 to about 40% of B, and the viscosity rating of the polymer being from about 3 to about 3000 cps; in which method, upon contact with the higher pH of the ocular fluid, said liquid formulation is converted to a stiff gel from which the ophthalmic treating agent is slowly released over a prolonged period of time.

2. A method according to claim 1 in which the ophthalmic treating agent is an ocular non-steroidal antiinflammatory drug, an ocular steroidal antiinflammatory agent, an ocular antibacterial agent, an ocular antifungal agent, an ocular antiviral agent, an anti-glaucoma agent, a miotic agent, an ocular decongestant, an antihistamine, a prostaglandin, a transdermal growth factor, an ocular nutrient or a demulcent.

3. A method according to claim 2 in which the non-steroidal antiinflammatory agent is diclofenac, flurbiprofen, suprofen, piroxicam or ketorolac, or an ophthalmologically acceptable salt thereof.

4. A method according to claim 2 in which the steroidal antiinflammatory agent is prednisolone acetate, prednisolone, fluorometholone, fluorometholone acetate, hydrocortisone, hydrocortisone acetate or dexamethasone.

5. A method according to claim 2 in which the antibacterial agent is chloramphenicol, ciprofloxacin, gentamycin, norfloxacin, sulfacetamide, tetracycline, tobramycin, vancomycin, ticarcillin, polymyxin B, penicillin G, neomycin, moxalactam, methicillin, kinamycin, gentamycin, erythromycin, colistimethate, clindamycin, cefazolin, carbenicillin, bacitracin, ampicillin or amikacin, or an ophthalmologically acceptable salt thereof.

6. A method according to claim 2 in which the antifungal agent is amphotericin B, flucytosine, natamycin or myconazole.

7. A method according to claim 2 in which the antiviral agent is idoxuridine, trifluridine, vidarabine, acyclovir or ganciclovir.

8. A method according to claim 2 in which the miotic agent is carbachol, pilocarpine, physostigmine, demecarium, echothiophate or isoflurophate, or an ophthalmologically acceptable salt thereof.

9. A method according to claim 2 in which the anti-glaucoma agent is dipivefrin, epinephrine, hydralazine, pilocarpine, carbachol, betaxolol, carteolol, lerobunolol, metipranolol, timolol, isosorbide, azetazolamide or methazolamide, or an ophthalmologically acceptable salt thereof.

10. A method according to claim 2 in which the ocular decongestant is naphazoline, phenylephrine or tetrahydrozoline, or an ophthalmologically acceptable salt thereof.

11. A method according to claim 2 in which the ocular nutrient is a form of Vitamin A comprising Vitamin A acid, Vitamin A alcohol, Vitamin A acetate or Vitamin A palmitate.

12. A method according to claim 1 in which the formulation has a pH between about 4.0 to about 6.0.

13. A method according to claim 1 in which the concentration of ophthalmic treating agent is from about 0.001% to about 10% by weight.

14. A method according to claim 1 in which the ophthalmic pharmaceutical composition comprises an osmotic agent and a preservative.

15. A method according to claim 14 in which the ophthalmic pharmaceutical composition also comprises a surfactant or wetting agent.

16. A sustained release liquid aqueous ophthalmic delivery system for an ophthalmic treating agent of a pH between about 3.0 to about 6.2, which comprises about 0.05% to about 10% by weight of the polymer chitosan as the release rate controlling agent, said polymer consisting essentially of
(A) monomeric β(1→4)-D-glucosamine linked units and
(B) monomeric β(1→4)-N-acetyl-D-glucosamine linked units which are scattered randomly in the molecule of the polymer, the numerical proportions of A and B being from about 60 to about 99% of A and about 1 to about 40% of B, and the viscosity rating of the polymer being from about 3 to about 3000 cps; said delivery system which is administrable in drop form being converted to a stiff gel on contact with the higher pH of the ocular fluid so as to provide a slow release into the eye for a prolonged period of time of the ophthalmic treating agent incorporated therein.

17. An ophthalmic delivery system of claim 16 in which said ophthalmic treating agent is present at a concentration of from about 0.001 to about 10% by weight.

18. An ophthalmic delivery system according to claim 17 which has an osmolality of about 240–340 mosmol/Kg and may further comprise an osmotic agent and a preservative.

19. An ophthalmic delivery system of claim 18 of pH between about 4.0 and about 6.0.

20. An ophthalmic delivery system according to claim 16 in which the ophthalmic treating agent is an ocular non-steroidal antiinflammatory drug, an ocular steroidal antiinflammatory agent, an ocular antibacterial agent, an ocular antifungal agent, an ocular antiviral agent, an anti-glaucoma agent, a miotic agent, an ocular decongestant, an antihistamine, a prostaglandin, a transdermal growth factor, an ocular nutrient or a demulcent 21. A liquid aqueous ophthalmic pharmaceutical composition of pH between about 3.0 and about 6.2, which is administrable in drop form, and which comprises about 0.05% to about 10% by weight of the polymer chitosan as the release rate controlling agent and an ophthalmic treating agent at an effective concentration; said polymer consisting essentially of
(A) monomeric β(1→4)-D-glucosamine linked units and of
(B) monomeric β(1→4)-N-acetyl-D-glycosamine linked units which are scattered randomly in the molecule of the polymer, the numerical proportions of A and B being from about 60 to 99% of A and about 1 to about 40% of B, and the viscosity rating of the polymer being from about 3 to about 3000 cps; said pharmaceutical composition upon contact with the higher pH of the ocular fluid being converted to a stiff gel so as to provide a slow release of the ophthalmic treating agent into the eye for a prolonged period of time.

* * * * *